United States Patent
Pigott

(10) Patent No.: US 11,033,712 B2
(45) Date of Patent: Jun. 15, 2021

(54) INTRAVASCULAR CATHETER HAVING AN EXPANDABLE PORTION

(71) Applicant: John P. Pigott, Sylvania, OH (US)

(72) Inventor: John P. Pigott, Sylvania, OH (US)

(73) Assignee: VentureMed Group, Inc., Plymouth, MN (US)

( * ) Notice: Subject to any disclaimer, the term of this patent is extended or adjusted under 35 U.S.C. 154(b) by 976 days.

(21) Appl. No.: 14/993,478

(22) Filed: Jan. 12, 2016

(65) Prior Publication Data

US 2016/0199617 A1     Jul. 14, 2016

Related U.S. Application Data

(60) Provisional application No. 62/102,747, filed on Jan. 13, 2015.

(51) Int. Cl.
*A61M 25/00* (2006.01)
*A61B 17/3207* (2006.01)
*A61B 17/00* (2006.01)

(52) U.S. Cl.
CPC . *A61M 25/0074* (2013.01); *A61B 17/320725* (2013.01); *A61B 2017/00986* (2013.01); *A61M 25/0097* (2013.01)

(58) Field of Classification Search
CPC ....... A61M 25/0074; A61B 17/320725; A61B 2017/00986
See application file for complete search history.

(56) References Cited

U.S. PATENT DOCUMENTS

| 2,655,154 A | 10/1953 | Richter |
| 3,500,789 A | 3/1970 | Wuebbeling |
| 3,557,794 A | 1/1971 | Van Patten |
| 3,704,711 A | 12/1972 | Park |
| 4,273,128 A | 6/1981 | Lary |
| 4,292,974 A | 10/1981 | Fogarty et al. |

(Continued)

FOREIGN PATENT DOCUMENTS

| EP | 0727194 A1 | 8/1996 |
| WO | 8102109 A1 | 8/1981 |

(Continued)

OTHER PUBLICATIONS

Cardiovascular Systems Inc., Diamondback 360 Coronary Orbital Atherectomy System, http://www.csi360.com/products/coronary-diamondback-360-coronary-orbital-atherectomy-system-crowns/, 2016.

(Continued)

*Primary Examiner* — Nathan R Price
*Assistant Examiner* — John A Doubrava
(74) *Attorney, Agent, or Firm* — Standley Law Group LLP

(57) ABSTRACT

An apparatus and method for the treatment of intravascular medical conditions is provided. The device comprising a handle assembly, an expandable portion defined by a plurality of struts oriented along a longitudinal axis and a tip member affixed to a distal end of the struts. The struts are moveable between a collapsed and an expanded position. A catheter tube extends from the handle assembly to the expandable portion. An elongate member is disposed within the catheter tube and is in communication with the handle assembly and the tip member.

12 Claims, 12 Drawing Sheets

(56) References Cited

U.S. PATENT DOCUMENTS

| | | |
|---|---|---|
| 4,654,027 A | 3/1987 | Dragan et al. |
| 5,030,201 A | 7/1991 | Palestrant |
| 5,074,871 A | 12/1991 | Groshong |
| 5,100,425 A | 3/1992 | Fischell et al. |
| 5,154,724 A | 10/1992 | Andrews |
| 5,156,610 A | 10/1992 | Reger |
| 5,178,625 A | 1/1993 | Groshong |
| 5,211,651 A | 5/1993 | Reger et al. |
| 5,224,945 A | 7/1993 | Pannek, Jr. |
| 5,244,619 A | 9/1993 | Burnham |
| 5,246,421 A | 9/1993 | Saab |
| 5,250,060 A | 10/1993 | Carbo et al. |
| 5,282,484 A | 2/1994 | Reger |
| 5,312,427 A | 5/1994 | Shturman |
| 5,318,576 A | 6/1994 | Plassche, Jr. et al. |
| 5,514,093 A | 5/1996 | Ellis et al. |
| 5,591,194 A | 1/1997 | Berthiaume |
| 5,658,309 A | 8/1997 | Berthiaume et al. |
| 5,665,098 A | 9/1997 | Kelly et al. |
| 5,676,654 A | 10/1997 | Ellis et al. |
| 5,697,944 A | 12/1997 | Lary |
| 5,697,948 A | 12/1997 | Marin et al. |
| 5,728,067 A | 3/1998 | Enger |
| 5,728,123 A | 3/1998 | Lemelson et al. |
| 5,733,296 A | 3/1998 | Rogers et al. |
| 5,792,158 A | 8/1998 | Lary |
| 5,800,450 A | 9/1998 | Lary et al. |
| 5,836,868 A | 11/1998 | Ressemann et al. |
| 5,876,448 A | 3/1999 | Thompson et al. |
| 5,961,536 A | 10/1999 | Mickley et al. |
| 5,968,064 A | 10/1999 | Selmon et al. |
| 6,071,287 A | 6/2000 | Verbeek |
| 6,120,515 A | 9/2000 | Rogers et al. |
| 6,129,708 A | 10/2000 | Enger |
| 6,165,187 A | 12/2000 | Reger |
| 6,217,549 B1 | 4/2001 | Selmon et al. |
| 6,258,108 B1 | 7/2001 | Lary |
| 6,270,489 B1 | 8/2001 | Wise et al. |
| 6,283,947 B1 | 9/2001 | Mirzaee |
| 6,527,740 B1 | 3/2003 | Jackson et al. |
| 6,599,267 B1 | 7/2003 | Ray et al. |
| 6,692,466 B1 | 2/2004 | Chow et al. |
| 6,695,863 B1 | 2/2004 | Ramzipoor et al. |
| 6,719,773 B1 | 4/2004 | Boucher et al. |
| 6,884,257 B1 | 4/2005 | Cox |
| 7,108,704 B2 | 9/2006 | Trerotola |
| 7,131,981 B2 | 11/2006 | Appling et al. |
| 7,279,002 B2 | 10/2007 | Shaw et al. |
| 7,303,572 B2 | 12/2007 | Melsheimer et al. |
| 7,329,267 B2 | 2/2008 | Weber |
| 7,517,352 B2 | 4/2009 | Evans et al. |
| 7,686,824 B2 | 3/2010 | Konstantino et al. |
| 7,691,086 B2 | 4/2010 | Tkebuchava |
| 7,708,753 B2 | 5/2010 | Hardert |
| 7,850,685 B2 | 12/2010 | Kunis et al. |
| 7,850,710 B2 | 12/2010 | Huss |
| 7,887,557 B2 | 2/2011 | Kelley et al. |
| 7,955,350 B2 | 6/2011 | Konstantino et al. |
| 8,323,307 B2 | 12/2012 | Hardert |
| 8,328,829 B2 | 12/2012 | Olson |
| 8,348,987 B2 | 1/2013 | Eaton |
| 8,366,661 B2 | 2/2013 | Weber et al. |
| 8,398,662 B2 | 3/2013 | Granada et al. |
| 8,454,636 B2 | 6/2013 | Konstantino et al. |
| 8,685,049 B2 | 4/2014 | Schur et al. |
| 8,685,050 B2 | 4/2014 | Schur et al. |
| 8,702,736 B2 | 4/2014 | Schur et al. |
| 8,740,849 B1 | 6/2014 | Fischell et al. |
| 8,870,816 B2 | 10/2014 | Chambers et al. |
| 9,079,000 B2 | 7/2015 | Hanson et al. |
| 9,192,747 B2 | 11/2015 | Hardert |
| 9,282,991 B2 | 3/2016 | Schur et al. |
| 9,314,329 B2 | 4/2016 | Dickinson et al. |
| 9,364,255 B2 | 6/2016 | Weber |
| 9,364,284 B2 | 6/2016 | Groff et al. |
| 9,510,901 B2 | 12/2016 | Steinke et al. |
| 9,532,798 B2 | 1/2017 | Schur et al. |
| 9,545,263 B2 | 1/2017 | Lenihan et al. |
| 9,592,386 B2 | 3/2017 | Mathur et al. |
| 9,604,036 B2 | 3/2017 | Burton et al. |
| 2001/0007059 A1 | 7/2001 | Mirzaee |
| 2002/0010489 A1 | 1/2002 | Grayzel et al. |
| 2002/0143350 A1 | 10/2002 | Heitzmann et al. |
| 2003/0069547 A1 | 4/2003 | Gonon |
| 2003/0125756 A1 | 7/2003 | Shturman et al. |
| 2003/0144677 A1 | 7/2003 | Lary |
| 2004/0034384 A1 | 2/2004 | Fukaya |
| 2004/0098014 A1 | 5/2004 | Flugelman et al. |
| 2004/0122457 A1 | 6/2004 | Weber |
| 2004/0204738 A1 | 10/2004 | Weber et al. |
| 2004/0267345 A1 | 12/2004 | Lorenzo et al. |
| 2005/0055077 A1 | 3/2005 | Marco et al. |
| 2005/0149102 A1 | 7/2005 | Radisch, Jr. et al. |
| 2005/0149159 A1 | 7/2005 | Andreas et al. |
| 2005/0151304 A1 | 7/2005 | Boelens et al. |
| 2005/0240176 A1 | 10/2005 | Oral et al. |
| 2006/0089637 A1 | 4/2006 | Werneth et al. |
| 2006/0111736 A1* | 5/2006 | Kelley ........... A61B 17/320725 606/159 |
| 2006/0116701 A1 | 6/2006 | Crow |
| 2006/0184191 A1 | 8/2006 | O'Brien |
| 2007/0005093 A1 | 1/2007 | Cox |
| 2007/0060863 A1 | 3/2007 | Goeken et al. |
| 2007/0106215 A1 | 5/2007 | Olsen et al. |
| 2007/0156225 A1 | 7/2007 | George et al. |
| 2007/0181157 A1 | 8/2007 | Dadourian |
| 2008/0140051 A1 | 6/2008 | Bei et al. |
| 2008/0294116 A1* | 11/2008 | Wolter ................. A61K 9/0021 604/173 |
| 2008/0300594 A1 | 12/2008 | Goto |
| 2008/0300610 A1 | 12/2008 | Chambers |
| 2009/0099583 A1 | 4/2009 | Butterfield et al. |
| 2009/0105686 A1 | 4/2009 | Snow et al. |
| 2009/0192508 A1 | 7/2009 | Laufer et al. |
| 2009/0204068 A1 | 8/2009 | Nguyen et al. |
| 2009/0306690 A1 | 12/2009 | Rivers et al. |
| 2009/0312807 A1 | 12/2009 | Boudreault et al. |
| 2010/0010521 A1 | 1/2010 | Kurrus |
| 2010/0121270 A1 | 5/2010 | Gunday et al. |
| 2010/0168737 A1 | 7/2010 | Grunewald |
| 2010/0168778 A1 | 7/2010 | Braido |
| 2010/0330147 A1 | 12/2010 | Hossainy et al. |
| 2011/0060182 A1* | 3/2011 | Kassab ............... A61B 17/3478 600/37 |
| 2011/0152683 A1 | 6/2011 | Gerrans et al. |
| 2011/0160645 A1 | 6/2011 | Sutermeister et al. |
| 2011/0184447 A1 | 7/2011 | Leibowitz et al. |
| 2011/0288479 A1* | 11/2011 | Burton ........... A61B 17/320725 604/103.08 |
| 2012/0053485 A1 | 3/2012 | Bloom |
| 2012/0143054 A1 | 6/2012 | Eaton et al. |
| 2012/0150142 A1 | 6/2012 | Weber et al. |
| 2012/0157988 A1 | 6/2012 | Stone et al. |
| 2012/0172901 A1* | 7/2012 | Manderfeld ...... A61M 25/1027 606/159 |
| 2013/0066346 A1* | 3/2013 | Pigott ............ A61B 17/320725 606/159 |
| 2013/0116715 A1* | 5/2013 | Weber ............ A61B 17/320725 606/159 |
| 2013/0131594 A1 | 5/2013 | Bonnette et al. |
| 2013/0150874 A1 | 6/2013 | Kassab |
| 2013/0237950 A1 | 9/2013 | Gianotti et al. |
| 2013/0253467 A1 | 9/2013 | Gianotti et al. |
| 2014/0277002 A1 | 9/2014 | Grace |
| 2014/0364896 A1 | 12/2014 | Consigny |
| 2015/0133978 A1 | 5/2015 | Paul, Jr. |
| 2017/0056048 A1 | 3/2017 | Erpen |
| 2017/0238960 A1 | 8/2017 | Hatta et al. |

FOREIGN PATENT DOCUMENTS

| | | |
|---|---|---|
| WO | 9502370 A2 | 1/1995 |
| WO | 1996039997 A2 | 12/1996 |

(56) References Cited

FOREIGN PATENT DOCUMENTS

| WO | 9918862 A1 | 4/1999 |
|---|---|---|
| WO | 02078511 A2 | 10/2002 |
| WO | 02078511 A3 | 10/2002 |
| WO | 2007095125 A2 | 8/2007 |
| WO | 2013159066 A1 | 10/2013 |
| WO | 2014106226 A2 | 7/2014 |
| WO | 2014142801 A1 | 9/2014 |
| WO | 2015190578 A1 | 12/2015 |
| WO | 2015195606 A1 | 12/2015 |
| WO | 2016210167 A1 | 12/2016 |

OTHER PUBLICATIONS

Boston Scientific, Rotablator Rotational Atherectomy System, http://www.bostonscientific.com/en-US/products/plaque-modification/rotablator-rotational-atherectomy-system.html, 2017.
International Search Report, Application No. PCT/US2012/055079, dated Jan. 31, 2013.
Boston Scientific Corporation, FilterWire EZ, Embolic Protection System for Carotid Arteries, Sep. 2015, http://www.bostonscientific.com/en-US/products/embolic-protection/filterwire-ez-embolic-protection-system.html.
Covidien, SpiderFX Embolic Protection Device, 2015, https://www.ev3.net/peripheral/us/embolic-protection/spiderfxtrade-embolic-protection-device.htm.
Boston Scientific, Sterling 0.018 Balloon Catheter, Jun. 2015.
Ham, S. et al., Safety of Carbon Dioxide Digital Subtraction Angiography, Archives of Surgery, Dec. 2011.
Alexander, J., $CO_2$ Angiography in Lower Extremity Arterial Disease, Endovascular Today, Sep. 2011, pp. 27-34.

\* cited by examiner

INTRAVASCULAR CATHETER HAVING AN EXPANDABLE PORTION

CROSS-REFERENCE TO RELATED APPLICATIONS

This application claims the benefit of U.S. Provisional Application No. 62/102,747, filed Jan. 13, 2015, the disclosure of which is incorporated herein by reference.

TECHNICAL FIELD

Exemplary embodiments of the present invention relate generally to devices and methods for intravascular catheters.

BACKGROUND AND SUMMARY OF THE INVENTION

This invention relates in general to intravascular catheters, such as can be used during minimally invasive surgical procedures. In particular, this invention relates to an intravascular catheter having an expandable incising portion.

Atherosclerosis is a chronic condition in which atheromatous plaque accumulates on the inner walls of a blood vessel. As a result, the blood vessel walls can become inflamed and, over time, may harden to form atherosclerotic lesions that cause a narrowing of the vessel lumen. In severe cases, the atherosclerotic lesions can rupture and induce the formation of thrombus (i.e., blood clots), which can prevent blood flow through the narrowed vessel lumen.

There are known procedures and devices for treating or otherwise reducing the risks associated with atherosclerosis. For example, an angioplasty is a procedure in which a balloon catheter is inserted into a narrowed region of the vessel lumen via a delivery catheter. The balloon catheter includes a flexible tube having an inflatable balloon at an end thereof. Once positioned in the narrowed region, the balloon is inflated in order to dilate the narrowed vessel lumen. The pressure in the balloon is generally sufficient to compress the accumulated plaque. However, in some cases it would be desirable to fragment the atherosclerotic lesions. Thus, it would be desirable to provide an intravascular catheter having an expandable portion that can be selectively controlled by a user and adapted to create incisions in atherosclerotic material to facilitate fragmentation of the material during an angioplasty procedure.

Additionally, endovascular surgery is a form of minimally invasive surgery that is used to diagnose and treat many diseases. Endovascular surgery requires the deployment of catheter devices containing medical treatment tools. These catheters can be inserted intravenously and manipulated to specific sites for medical intervention. This form of minimally invasive surgery is becoming an ever more popular surgical technique due to reduced side effects such as scarring and infection. Examples of endovascular surgery include aneurysm repair, angioplasty, and carotid stenting. Endovascular surgical techniques are utilized by radiologists, neurologists, neurosurgeons, cardiologists, and vascular surgeons, among other medical professionals. Endovascular surgeons would benefit from a stable, maneuverable catheter platform device that can be used to deliver medical treatment.

This invention relates to an intravascular catheter device for use during a surgical procedure. The catheter device includes a catheter tube having an expandable portion with a plurality of struts each defining an outer surface. The expandable portion is operable between a closed position, wherein the expandable portion has a first diameter, and an opened position, wherein the expandable portion has a second diameter that is larger than the first diameter. An incising element is provided on the outer surface of at least one of the struts. The incising element has a blade that extends outwardly in a radial direction from the outer surface of the strut for creating an incision in atherosclerotic material located within a blood vessel when the expandable portion is in the opened position.

The present invention additionally relates to a catheter platform device for use during endovascular surgery. The expandable portion is configured to provide a stable, flexible platform for medical treatment. The distal end of the catheter, including the expandable portion and the surrounding non-expandable portion, is capable of receiving a plurality of various medical treatment tools.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENTS

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1:
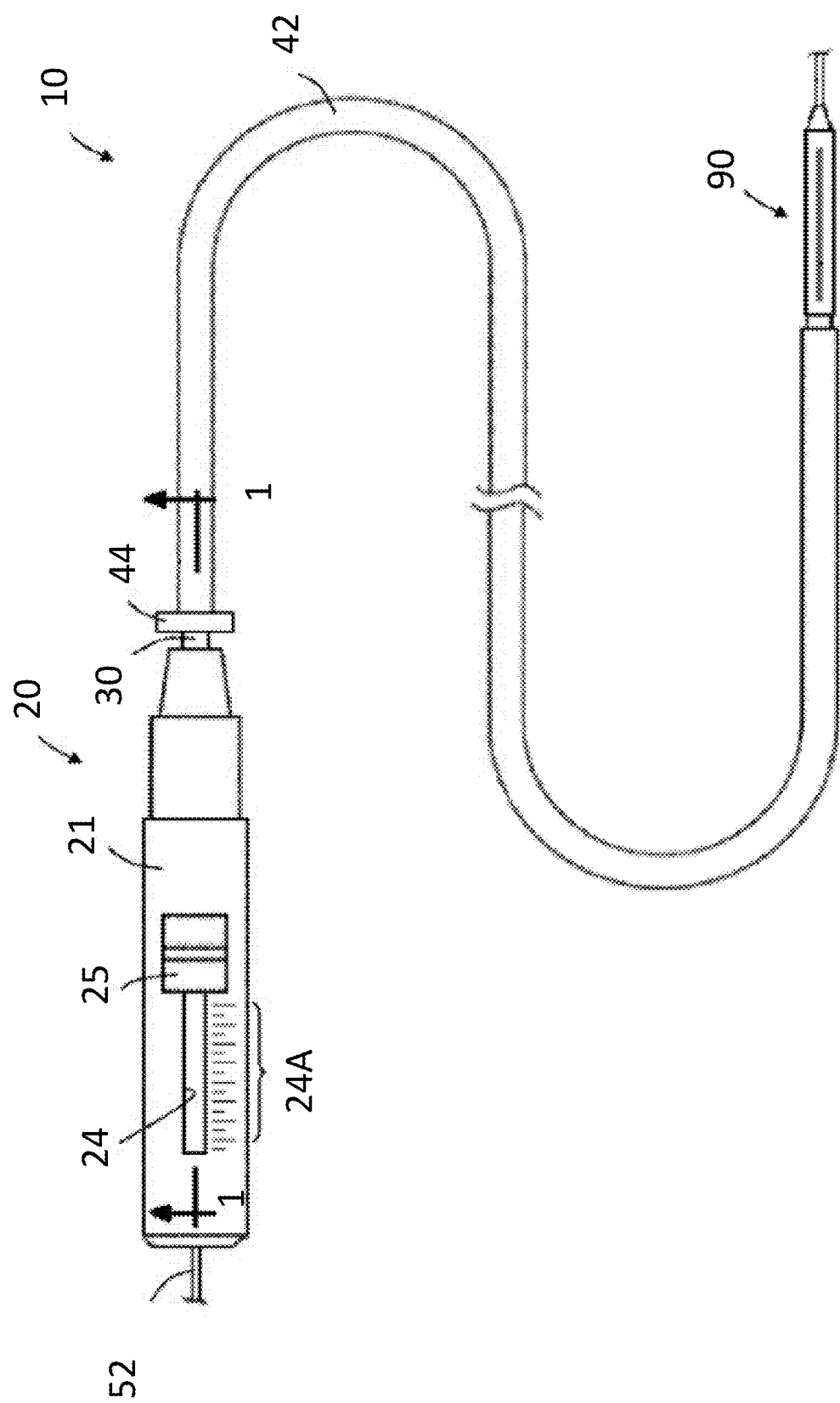
FIG. 1 is a plan view of another exemplary embodiment of the catheter device.

Referring now to the drawings, there is illustrated in FIG. 1 a catheter device, indicated generally at 10, in accordance with the present invention. The illustrated catheter device 10 is configured to treat or reduce the risks associated with various medical ailments by providing a stable, expandable platform for the performance of endovascular surgery, which may include the introduction of medical treatment devices. In general, the catheter device 10 includes an expandable portion on the distal end of the catheter, indicated generally at 90, which can be inserted into a blood vessel and expanded to create a stable platform. This stable platform can be configured to receive a plurality of medical treatment devices that may be manipulated by operating the catheter device.

Although the present invention will be described in the context of a number of embodiments, some of which may have particular medical applications, it should be appreciated that the present invention can be used in any desired environment and for any desired purpose.

The illustrated catheter device 10 includes a handle assembly, indicated generally at 20. The illustrated handle assembly 20 includes an elongated, cylindrical handle body 21. The handle body 21 may alternatively have any other shape that is suitable for easy handling by a surgeon. Further, the handle body 21 can be made from any suitably rigid material including, but not limited to, stainless steel or polymers. The handle assembly 20 is configured to selectively control the expansion and contraction of the expandable portion 90 by operation of a control mechanism 25. In the present embodiment, the control mechanism is shown as a slide that operates in slot 24. The slide permits the surgeon to operate the control mechanism 25 along the slot 24 in the handle body 21. This mechanism will be described in greater detail in the proceeding sections.

Additionally, the handle body 21 contains an information display that indicates information about the expandable portion 90. In the present embodiment, the information display takes the form of graduated marks 24A on the handle body 21. In the present embodiment, the graduated marks correspond to and indicate the diametric expansion of the expandable portion 90. In the present embodiment, the slide is configured to be operated by the surgeon's thumb and may be any shape that is suitable for easy thumb operation by a surgeon.

Other embodiments of the control mechanism 25 may include, but are not limited to, a knob, lever, or electronically controlled motor, or any other known device configured to permit the surgeon to control the expansion and contraction of the expandable portion 90. Other embodiments of the display include, but are not limited to, numbers, other markings and digital displays. Other information that may be displayed includes, but is not limited to, the status and location information of any attached medical treatment devices and protective sheaths.

The catheter device 10 also contains a catheter tube 30. The catheter tube is attached to and is in communication with the interior cavity of the handle body 20 and extends to and is in communication with the interior cavity of the expandable portion 90. The catheter tube 30 may be secured to the handle body 20 using a flanged connection, a fused connection, an adhesive, a press fit connection, a threaded connection, or any other securing means. Alternatively, the catheter tube 30 may be secured to the handle body 20 using a connector or any other type of attachment device. The catheter tube 30 can have any outer diameter, length, or wall thickness. The catheter tube 30 may be secured to the expandable portion 90 using a flanged connection, a fused connection, an adhesive, a press fit connection, a threaded connection, or any other securing means. Alternatively, the catheter tube 30 may be secured to the expandable portion 90 using a connector or any other type of attachment device. The catheter tube 30 may further be configured to facilitate communication between the control mechanism 25 and the expandable portion 90 via an inner lumen that allows the passage of control and communication means, such as wire. The inner lumen of catheter tube 30 is further configured for sliding movement along an outer surface of a guide wire 52. This will be further explained in the proceeding sections.

The catheter tube 30 may extend through a protective sheath 42 that is configured for sliding movement along an outer surface of the catheter tube 60. The protective sheath 42 can be made from any biocompatible material including, but not limited to, polyvinyl, polyethylene, nitinol, or stainless steel. Further, the protective sheath 42 can have any outer diameter, length, or wall thickness suitably configured for sliding along an outer surface of the catheter tube 60.

The protective sheath 42 includes a flange 44 that facilitates sliding movement of the protective sheath 42 relative to the catheter tube 30. The flange 44 is an annular member located at the proximal end of the protective sheath 42 nearest the handle assembly 20. The flange 44 may be integrally formed with the protective sheath 42 or may otherwise be secured thereto in any manner, such as by an adhesive, threaded connection, or any other suitable attachment means. It should be appreciated that the flange 44 can have any shape or may alternatively be configured in any manner to accomplish the functions described herein and below.

The catheter device 10 may be guided into position by use of a guide wire 52. The guide wire 52 is inserted intravenously by the surgeon and manipulated through the blood vessels to a desired site. The catheter device 10 may then be inserted over the guide wire 52, specifically such that the inner lumen of catheter tube 30 surrounds the guide wire 52. The catheter device 10 may then be further inserted, following the guide wire 52, until the catheter device 10 is properly located intravenously at the desired site. The surgeon may further manipulate the position of the expandable portion 90 at any time by further retracting or extending the catheter tube 30, optionally including protective sheath 42, along guide wire 52. Alternatively, the surgeon may further manipulate the position of the expandable portion 90 by pulling on or further extending the handle assembly 20.

Figure 2:
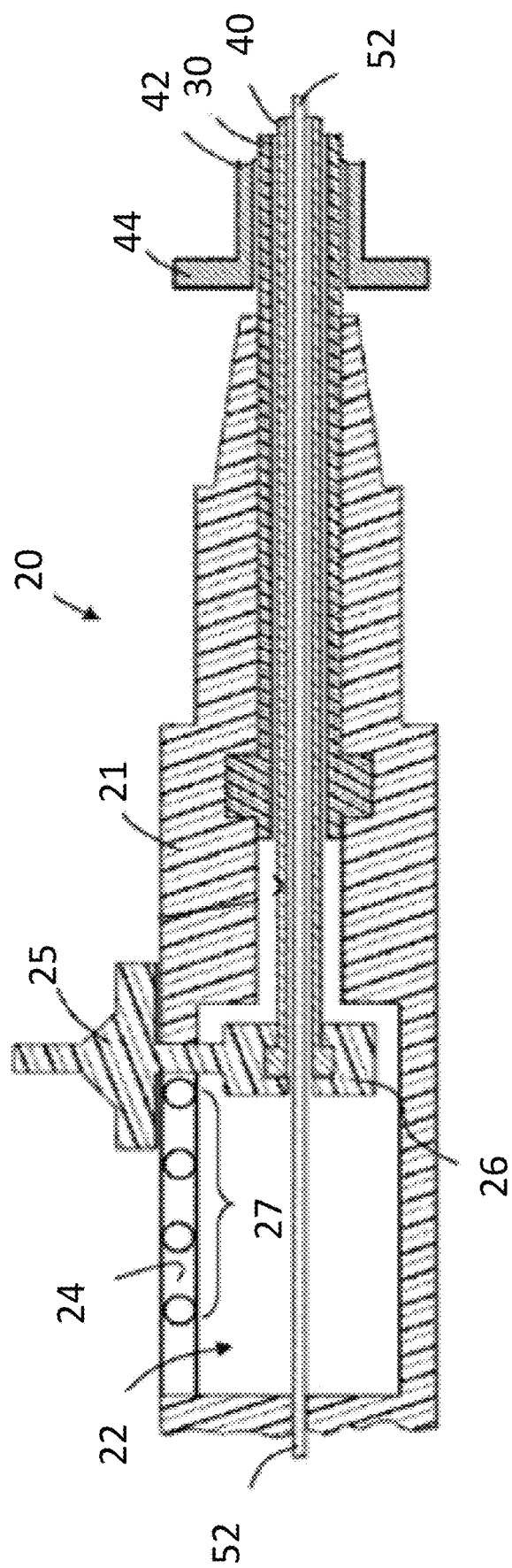
FIG. 2 is a cross-section end view of the device of FIG. 1 taken along section line 1-1 with the sliding mechanism located in the forward position relative to the expandable portion.

Referring now additionally to FIG. 2, the handle assembly 20 is enlarged and shown in a cross sectional view along section line 1-1. The handle body 21 defines an interior chamber, indicated generally at 22. The control mechanism 25 is embodied in the present illustration as a slide mechanism. A portion of the slide mechanism 26 protrudes vertically into the interior chamber 22 and surrounds the guide wire 52, control member 40, and catheter tube 30. The portion of the slide mechanism 26 is configured to permit the guide wire 52 to pass through horizontally and slide along an outer surface thereof. The control member 25 passes into the slide mechanism portion 26 and is configured to terminate and be secured therein such that the slide mechanism portion 26 is in communication with the control member 25 and when the control member 25 is operated by the surgeon, the control member 26 is likewise manipulated. In the present embodiment, when the slide mechanism is advanced along slot 24, the control member 25 is likewise advanced relative to the handle 20.

The catheter tube 30 is terminated in the handle body 21 such that the catheter tube 30 is secured to and in communication with the handle body 21. The catheter tube 30 is secured such that manipulation of the handle body 21 results in the likewise manipulation of the catheter tube 30. The catheter tube 30 is configured such that it can slide along an outer surface of the inner tube 40 and guide wire 52.

The slide mechanism 30 can be temporarily secured into a number of positions by the use of locking devices 27. In the present embodiment, the locking devices 27 are located in the exterior wall of the handle body 21 in the slot 24 of the aperture configured for the control member 25 and the portion 26 to extend into the interior chamber 22. In the present embodiment, the locking mechanism 27 is illustrated as a series of protrusions that are spaced apart from one another along the inner surface of the slot 24. The control member 25 frictionally engages the protrusions 27 to temporarily secure the control member 25 in a desired position. Alternatively, the locking mechanism 27 may be a threaded fastener, a pivotal latch, a push-button release, or any other mechanism that is configured to temporarily secure the control member 25 in a desired position.

The optional protective sheath 42 surrounds the catheter tube 30 and includes annual member 44 configured to slide over the catheter tube 30.

FIG. 2 corresponds to the expandable portion 90 being operated in the closed position as the control member 25 is located proximally to the expandable portion 90. Correspondingly, the control member 25 is advanced proximally relative to the expandable portion 90. The operation of the control member 25 and the expandable portion 90 will be explained further in the proceeding sections.

Figure 3:
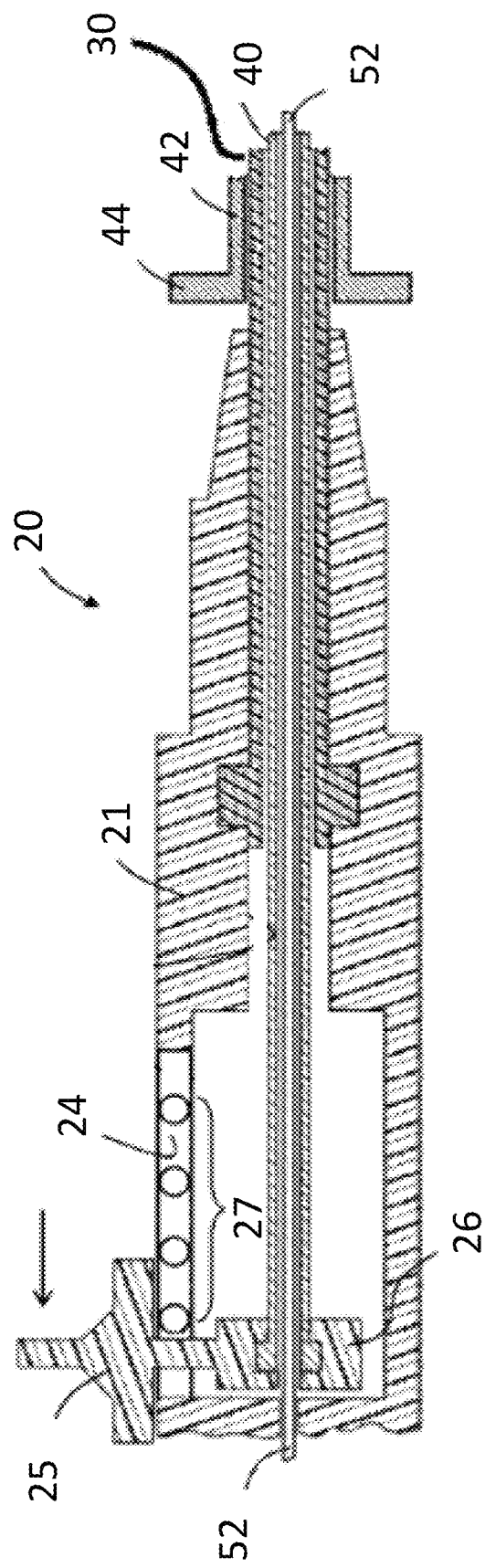
FIG. 3 is a cross-section end view of the device of FIG. 1 taken along section line 11-11 with the sliding mechanism retracted to the read position relative to the expandable portion.

The structure of the device pictured in FIG. 3 corresponds to that of the device pictured in FIG. 2, where FIG. 3 corresponds to the expandable portion 90 being operated in the open position. As indicated by the arrow in the present figure, the control member 25 and portion 26 are located distally relative to expandable portion 90. The operation of the control member 25 and the expandable portion 90 will be explained further in the proceeding sections.

Figure 4:
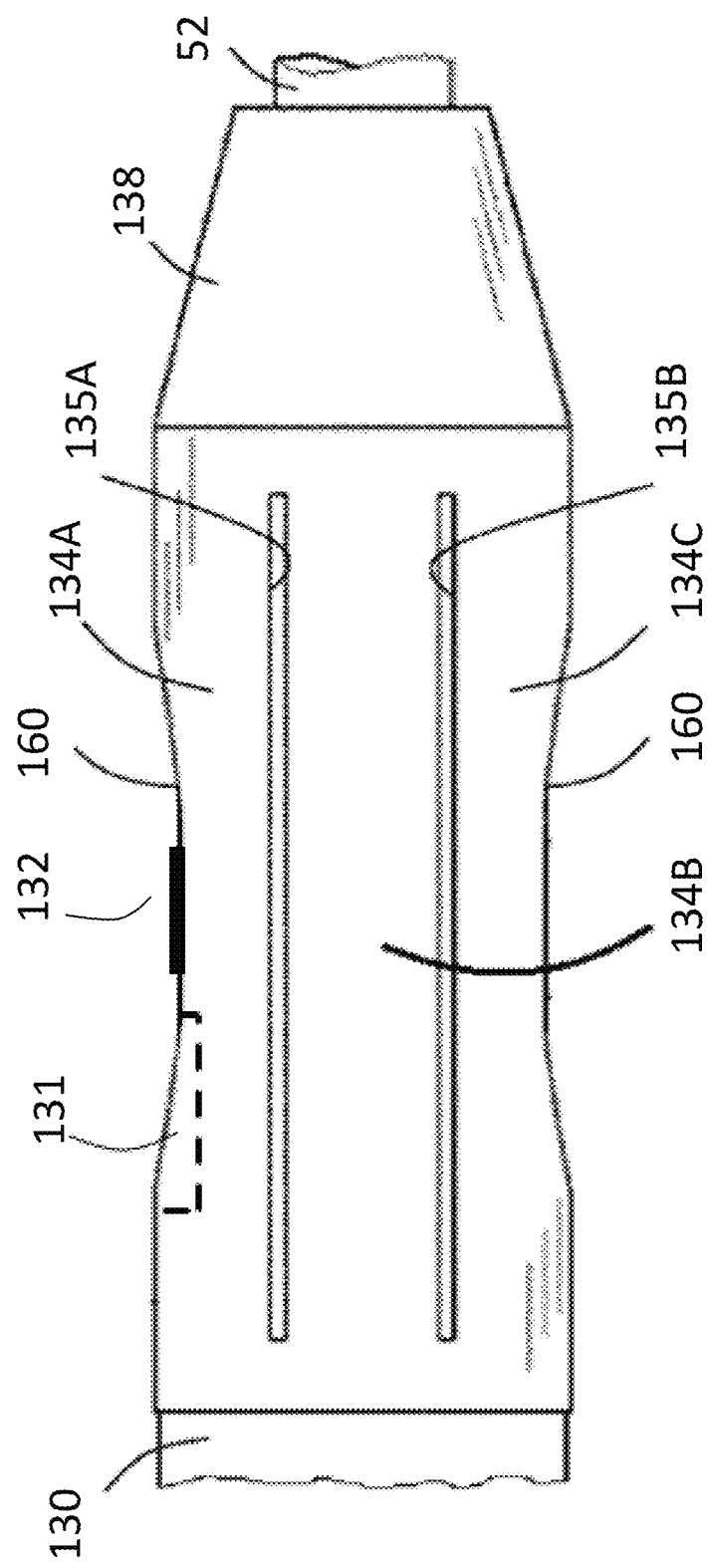
FIG. 4 is an enlarged side view of the distal end of the catheter, with the expandable portion in a closed position.
Figure 5:
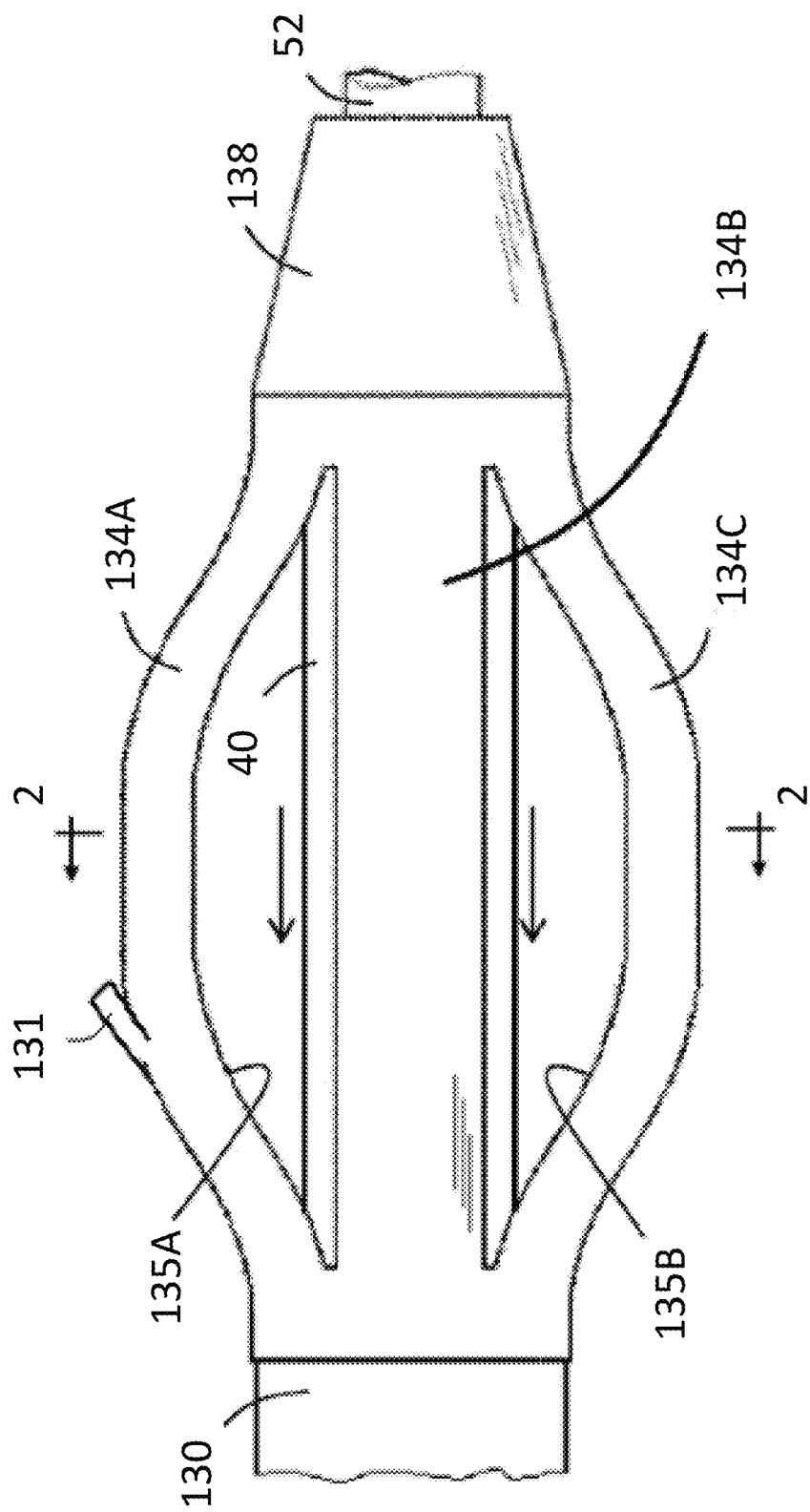
FIG. 5 is the device of FIG. 4 with the expandable portion expanded in an open position.
Figure 7:
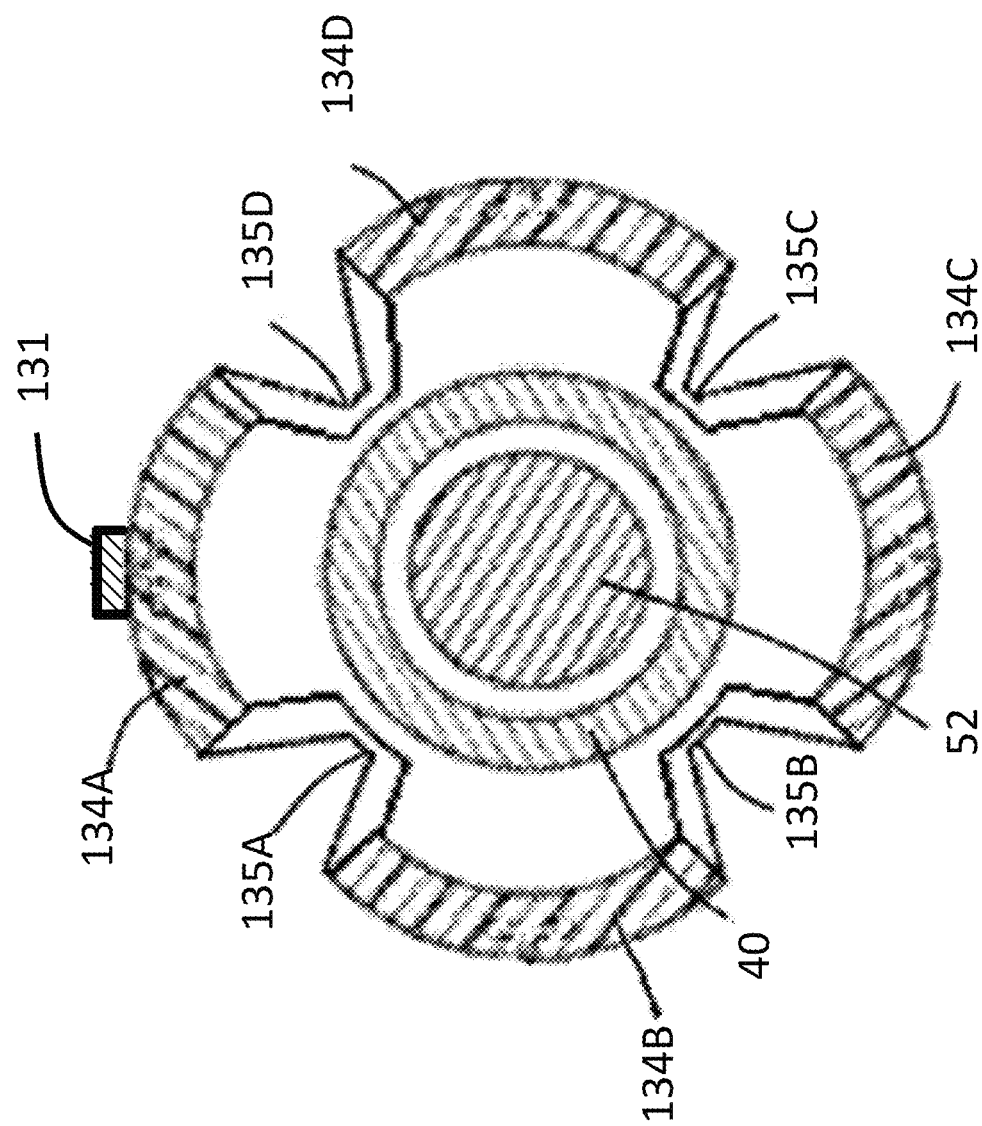
FIG. 7 is a cross-section end view of the device of FIG. 5 taken along section line 2-2.

Referring now to FIGS. 4 and 5, the expandable portion 90 may be defined by a plurality of outer struts, illustrated herein as 134A, 134B, 134C, and 134D, which may be separated by longitudinally extending slits 135A, 135B, 135C, and 135D (135C and 135D are illustrated in FIG. 7). In the present embodiment, the expandable portion is defined by four struts terminated in an end cap 138. The end cap 138 may be in communication with the control member 40. Alternative embodiments are contemplated that contain any number of a plurality of struts. As illustrated in the figure, the struts may contain an elongated depression, as can be seen at 160, near the midpoint of struts 134A and 134B. An elongated depression may be located on the other struts, but is not visible in the present figures. The elongated depressions 160 may be configured such the depressed area remains substantially parallel to guide wire 152 when the expandable portion is in the open position. The elongated depressions 160 may be configured to receive a medical treatment device 131. In other exemplary embodiments of the present invention, there may be no such depression or there may be an elevation.

The struts 134A, 134B, 134C, and 134D, may be configured to receive a plurality of medical treatment device attachments 131. An attachment device 132 may be located on at least one of the struts 134A, 134B, 134C, or 134D to facilitate the attachment of the medical treatment device 131. The attachment device 132 may be a clamp, magnet, clip, mated fastener, corresponding slot or groove, or any other attachment means for facilitating the attachment of the medical treatment device 131. In exemplary embodiments, the elongated depression 160 or the strut 134A, 134B, 134C, or 134D may also serve as the attachment device 132 or the attachment device 132 may be integrated with the strut 134A, 134B, 134C, or 134D. In still other exemplary embodiments, the attachment device 132 may not be required, as the medical treatment device 131 may be integrated with the strut 134A, 134B, 134C, or 134D.

In an exemplary embodiment, the medical treatment device may be an atherectomy tool, which may be attached to the outer strut 134A. The atherectomy tool may be a straight line appendage. In other embodiments, the atherectomy tool may be an arcuate blade, or other shape configured for atherectomy. The atherectomy tool may be configured such that when the expandable portion 90 is in the closed position, the atherectomy tool lays substantially flush with the outer surface of the outer strut 134A. The medical treatment devices may include, but are not limited to, drug delivery devices including needles or targeted delivery systems, incising and scoring elements, heating and cooling elements such as cauterizing and ablation devices, diagnostic devices such as biopsy and imaging tools, and surgical devices such as cutting devices, clamps, and stitching tools. Skilled artisans will appreciate that this list is merely exemplary and that other medical device attachments may be utilized with the present invention and other embodiments of the present invention may be realized. In exemplary embodiments, the medical treatment device 131, such as but not limited to the atherectomy tool, may extend beyond the outer diameter of the expandable portion 90 when the expandable portion 90 is in the open position.

Figure 6:
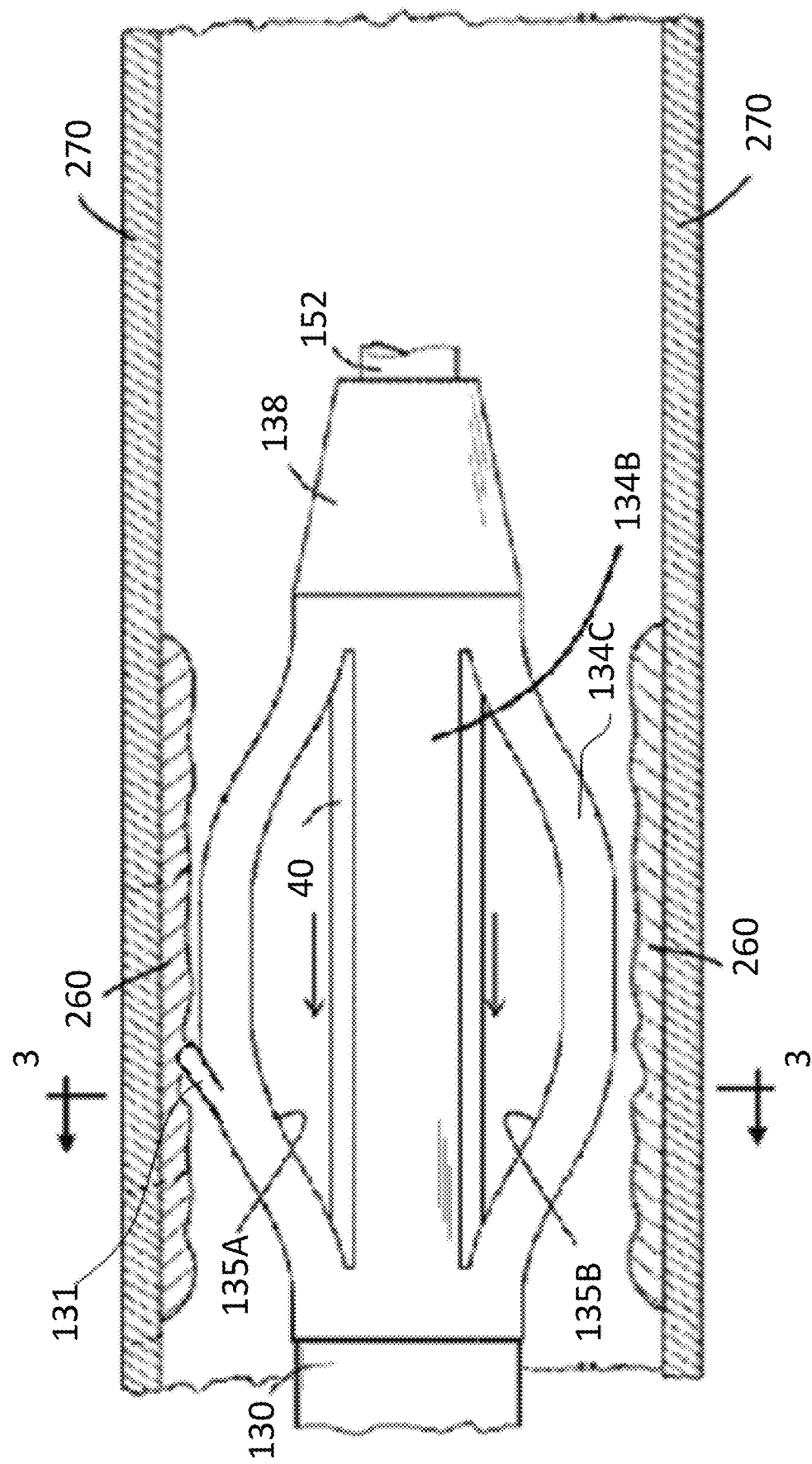
FIG. 6 is the device of FIG. 5 illustrated inside a blood vessel having atheromatous plaque accumulation.
Figure 8:
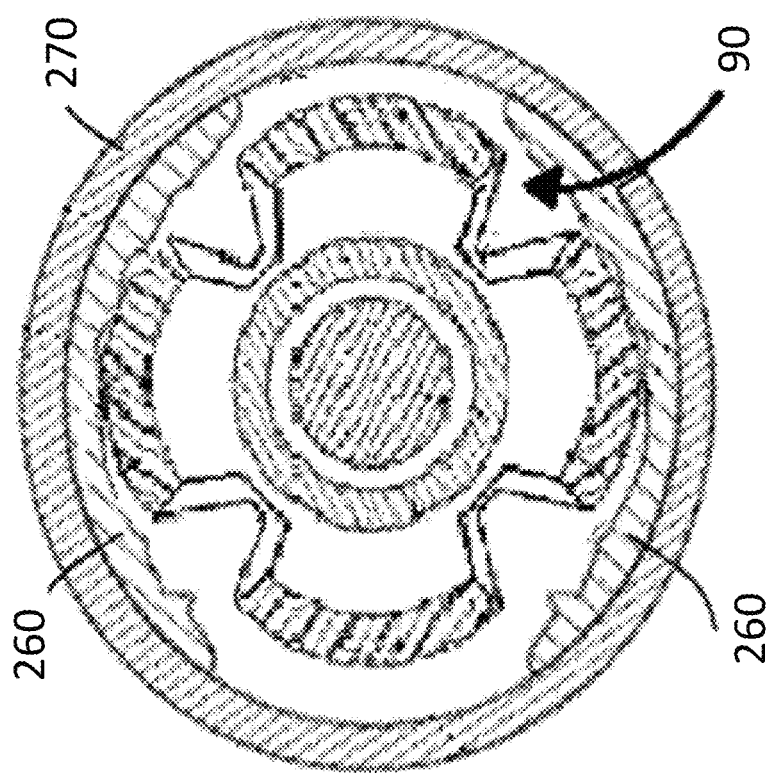
FIG. 8 is a cross-section end view of the device of FIG. 6 taken along section line 3-3.

Referring to FIG. 6 and FIG. 8, the device is illustrated in the open position as located inside a blood vessel 270. The struts 134A, 134B, 134C, and 134D are illustrated as being located in contact with or near to the atheromatous plaque accumulation 260 along the blood vessel walls 270. The expandable portion 90 may be moved along the blood vessel 270 while in the open or closed position by further inserting or retracting the catheter tube 130 by inserting or retracting the handle 20 as manipulated by the user. In exemplary embodiments the medical treatment device 131, such as but not limited to the atherectomy tool, may protrude into the atheromatous plaque accumulation 260 along the blood vessel walls 270. The device may be further inserted or retracted along blood vessel 270 to facilitate the excise of the atheromatous plaque accumulation 260 by atherectomy tool. In other exemplary embodiments, the device 10 may otherwise treat the atheromatous plaque accumulation 260. In still other exemplary embodiments, the device 10 may otherwise treat the blood vessel 270 not necessarily containing the atheromatous plaque accumulation 260. As previously discussed, other medical tools are expressly contemplated.

Referring to FIG. 7 and FIG. 8, a cross section of the expandable portion 90 of the catheter device 10, is shown in the open position. The cross section is taken along section line 12-12 of FIG. 5. In FIG. 8, the device of FIG. 7 is illustrated as located inside a blood vessel 270. The struts 134A, 134B, 134C, and 134D, are illustrated as being located in contact with or near to the atheromatous plaque accumulation 260 along the blood vessel walls 270. Alternatively, the struts 134A, 134B, 134C, and 134D may be expanded in order to place a medical treatment device attachment 131 (not pictured in the present figures) in contact with or near to the blood vessel wall 270. The expandable portion 90 may be moved along the blood vessel 270 while in the open or closed position by further inserting or retracting the catheter tube 130 by inserting or retracting the handle as manipulated by the user.

Figure 9:
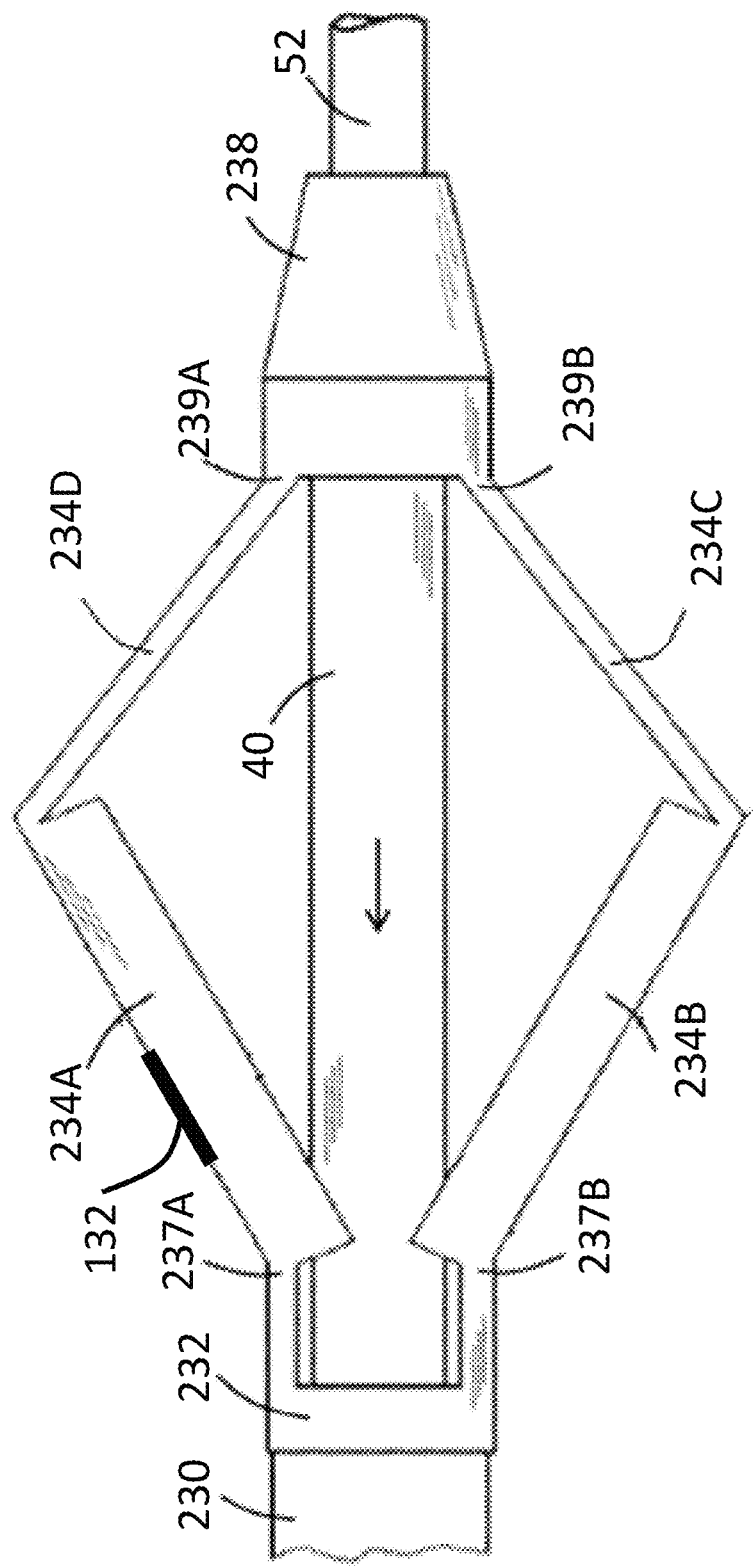
FIG. 9 is another exemplary embodiment of the present invention illustrating a side view of the distal end of the catheter, expanded into an open position.
Figure 10:
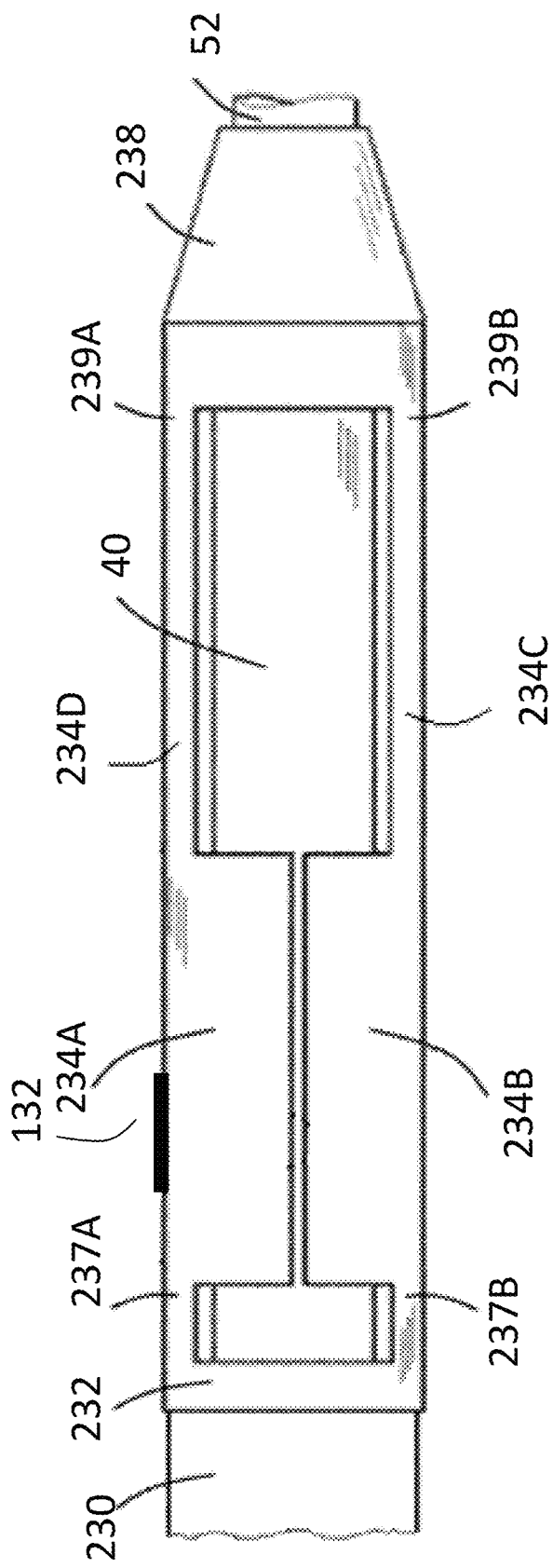
FIG. 10 contains a side view of the device of FIG. 9 with the expandable portion in a closed position.
Figure 11:
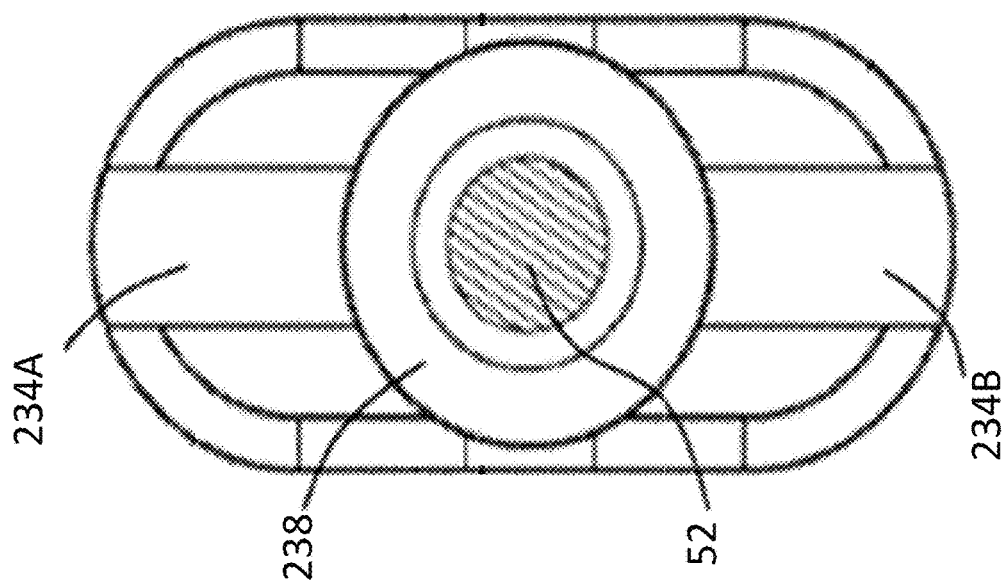
FIG. 11 is an end view of the device of FIG. 9.

Referring to FIG. 9 through FIG. 11, another exemplary embodiment of the present invention is illustrated. These figures illustrate the expandable portion 90 of the catheter device 10 with the struts 243A, 234B, 234C, and 234D embodied as flat, rigid surfaces. In the present embodiment, the struts 243A, 234B, 234C, and 234D make up two outer struts. The outer struts are each comprised of two beams; the beams 234D and 234A, comprising one strut, while the beams 234B and 234C comprise the other strut. The outer beams may be attached together and to the catheter tube 230 by a joining section 232. The joining section 232 may be attached to catheter tube 230 by a threaded fastener, adhesive, or be formed as one piece. The outer beams may be joined to the joining section 232 by the weakened regions or pivoting means 237A and 237B or alternatively be formed as one piece. Likewise, on the distal end of the expandable portion 90, the outer beams may be joined to the tip member 238 by the weakened regions or pivoting means 237A, 237B, 239A, and 239B or alternatively be formed as one piece.

It should be appreciated that any number of outer struts and corresponding beams may be utilized. Additionally, the struts are attached to the tip member 238 and may be attached by a threaded fastener, an adhesive, a press fit, or other attachment means.

Like the previous exemplary embodiments, the outer beams may be configured to receive and manipulate any medical treatment devices 131.

Figure 12:
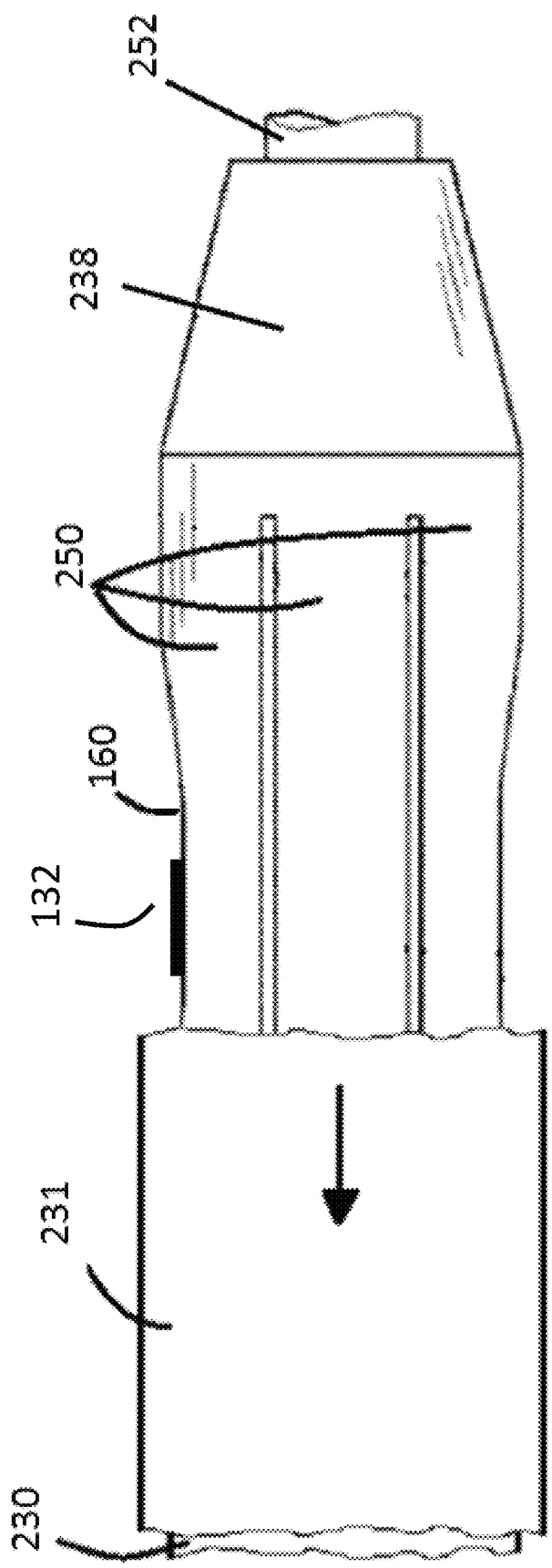
FIG. 12 is a side view of another exemplary embodiment of the device of FIG. 4 with the expandable portion in a closed position and a sheath partially retracted.

Referring now to FIG. 12, another exemplary embodiment of the present invention is illustrated. A protective sheath 231 surrounds the expandable portion 90 of the device 10. The protective sheath 231 may be of any thickness. The protective sheath 231 may surround the expandable portion 90 and the catheter tube 230 until the protective sheath 231 is withdrawn by the user. The protective sheath 231 may be withdrawn relative to the expandable portion 90 by operation of the handle 20. The protective sheath 231 may be operated via a linkage in communication with said handle 20 via the catheter tube 100. The linkage may be mechanical or electrical.

In certain embodiments of the present invention, the outer struts, referred to collectively here as 250, may contain no bias to expand or collapse, and their expansion and contraction is operated by the same mechanisms as previously described herein. In other exemplary embodiments, the outer struts 250 may be made of a suitable material, such as spring steel, such that they are biased in the expanded position.

In another exemplary embodiment, the outer struts 250 of the expandable portion 90 are biased in the expanded position. When the protective sheath 231 is retracted, as indicated by the arrow in the figure, the outer struts 250 are permitted to expand into an open position. Likewise, when the protective sheath 231 is extended relative to the expandable portion 90, in the opposite direction of the arrow indication, the outer struts 250 are forced into a collapsed position. The protective sheath 231 may also serve to enclose and protect the outer struts 250. Further, the protective sheath 320 may also be configured to enclosure and protect an attached medical device 131 if one is utilized with the present invention.

While the present embodiment is illustrated with the device of FIG. 4, it should be appreciated that the protective sheath 231 may be utilized with any of the embodiments disclosed herein.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A method for providing intravascular medical treatment comprising the steps of:
    providing an intravascular device for medical treatment comprising a handle assembly comprising a control member, an expandable portion comprising a plurality of struts oriented with a longitudinal axis of the expandable portion and configured to move between a collapsed position and an expanded position, a tip member affixed to a distal end of said struts, a catheter tube extending from the handle assembly to the expandable portion and defining an inner lumen, a linkage disposed within the inner lumen and connected to the control member at a first end thereof and the tip member at a second end thereof, an attachment device located on at least one of the plurality of struts where said attachment device is configured to permit the selective interchangeability of one of a number of medical tools, and a recessed portion located at the at least one of the plurality of struts having the attachment mechanism located thereon, wherein the recessed portion is adapted to provide a substantially flat surface when the expandable portion is in the expanded position at the location where the attachment device is mounted to the at least one of the plurality of struts such that the attachment device remains substantially parallel with a longitudinal axis of the expandable portion when the expandable portion is in the expanded position;
    selecting one of the number of medical tools for attachment, wherein the medical tool is selected to provide a particular therapeutic or diagnostic effect when utilized at a zone of treatment;
    attaching the selected medical tool to the expandable portion by way of the attachment device;
    placing the expandable portion in the collapsed position;
    manipulating the expandable portion to the zone of treatment within the person's vascular system;
    placing the expandable portion into the expanded position;
    utilizing the selected medical tool at the zone of treatment;
    placing the expandable portion into the collapsed position; and
    removing the expandable portion from the person's vascular system.

2. The method of claim 1 further comprising the steps of:
    providing a guide wire;

manipulating the guide wire to the zone of treatment within the person's vascular system; and disposing the intravascular device atop the guide wire.

3. The method of claim 1 further comprising the steps of:

selecting a second one of the number of medical tools for attachment, wherein the second medical tool is selected to provide a particular therapeutic or diagnostic effect when utilized at the zone of treatment; and attaching the second medical tool to the expandable portion by way of the attachment device.

4. The method of claim 1 wherein:

the number of medical tools is selected from a group consisting of: a diagnostic device, a drug delivery device, an atherectomy device, an incising element, a heating or cooling element, and a surgical device.

5. An apparatus for providing intravascular medical treatment comprising:

an expandable portion comprising a plurality of struts oriented with a longitudinal axis of the expandable portion and configured for movement between a collapsed position and an expanded position;

a catheter tube extending from the expandable portion;

an attachment device located on one of the struts and configured to selectively receive, in an interchangeable fashion, one of a number of medical tools, wherein each of said number of medical tools are configured to provide a different medical effect at a zone of attention within a person's vascular system; and an inner tube connected to said expandable portion and configured to effectuate movement of the expandable portion between the collapsed and expanded positions upon movement of said inner tube.

6. The apparatus of claim 5 further comprising:

a handle assembly, wherein said catheter tube extends between said handle assembly and said expandable member;

a control mechanism located at said handle assembly and connected to said inner tube; and an end cap connecting a distal end of each of said struts to said inner tube.

7. The apparatus of claim 6 wherein:

the attachment device is adapted to provide a substantially flat surface that remains substantially parallel to a longitudinal axis of the expandable portion upon movement of the expandable portion into the expanded position.

8. The apparatus of claim 7 wherein:

the number of medical tools comprise is selected from a group consisting of: a diagnostic device, a drug delivery device, an atherectomy device, an incising element, a heating or cooling element, and a surgical device.

9. The apparatus of claim 8 further comprising:

a recessed portion located on the one strut having the attachment mechanism located thereon, wherein said recessed portion is provided at a location of the attachment mechanism and is adapted to provide a flat surface when the expandable portion is in the expanded position.

10. A method for providing intravascular medical treatment comprising the steps of:

providing an intravascular device for medical treatment comprising a handle assembly comprising a control device, an expandable portion comprising a plurality of longitudinally extending struts, a tip member connected to a distal end of each of said struts, a catheter tube extending from the handle assembly to the expandable portion and defining an inner lumen, a linkage disposed within the inner lumen and connected to the control device at a first end thereof and the tip member at a second end thereof, an attachment device located at one of the struts and configured to interchangeably receive one of a number of different types of medical tools;

selecting one of the number of medical tools, wherein the medical tool is selected to provide a particular therapeutic or diagnostic effect at a zone of treatment;

securing the medical tool to the attachment device;

manipulating the control device to place the expandable portion in the collapsed position such that said struts extend along said linkage;

manipulating the expandable portion to the zone of treatment;

placing the expandable portion into the expanded position such that said struts bow outwardly;

utilizing the medical tool at the zone of treatment;

manipulating the control device to place the expandable portion in the collapsed position a second time; and removing the expandable portion from the person's vascular system.

11. The method of claim 10 wherein:

said intravascular device comprises a recessed portion located at the strut having the attachment mechanism located thereon at a location of the attachment mechanism; and the recessed portion is adapted to provide a flat surface when the expandable portion is in the expanded position at the location where the attachment device is mounted to the one of the struts such that the attachment device remains parallel with a longitudinal axis of the expandable portion when the expandable portion is in the expanded position.

12. The method of claim 10 wherein:

the number of medical tools is selected from the group consisting of: a diagnostic device, a drug delivery device, an atherectomy device, an incising element, a heating or cooling element, and a surgical device.

* * * * *

UNITED STATES PATENT AND TRADEMARK OFFICE
CERTIFICATE OF CORRECTION

Page 1 of 1

PATENT NO. : 11,033,712 B2
APPLICATION NO. : 14/993478
DATED : June 15, 2021
INVENTOR(S) : John P. Pigott It is certified that error appears in the above-identified patent and that said Letters Patent is hereby corrected as shown below:

On the Title Page

Item (56) In the References Cited Column 2:
Please delete "3,500,789 A 3/1970 Wuebbeling" and insert --8,500,789 B2 8/2013 Wuebbeling et al.--.

In the Claims

In Claim 8, Column 9, Line 2:
Please delete "comprise".

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*